US005997868A

United States Patent [19]
Goldberg et al.

[11] Patent Number: 5,997,868
[45] Date of Patent: Dec. 7, 1999

[54] INHIBITION OF SCATTER FACTOR FOR BLOCKING ANGIOGENESIS

[75] Inventors: Itzhak D. Goldberg, Englewood, N.J.; Eliot M. Rosen, Port Washington, N.Y.

[73] Assignee: North Shore University Hospital Research Corporation, Manhasset, N.Y.

[21] Appl. No.: 09/052,199

[22] Filed: Mar. 31, 1998

Related U.S. Application Data

[63] Continuation of application No. 08/746,636, Nov. 13, 1996, Pat. No. 5,837,676, which is a continuation of application No. 08/138,667, Oct. 18, 1993, abandoned.

[51] Int. Cl.[6] .................................................. A61K 39/395
[52] U.S. Cl. ...................... 424/158.1; 530/351; 530/399
[58] Field of Search .................................. 530/399, 351; 424/158.1

[56] References Cited

U.S. PATENT DOCUMENTS

| 5,268,384 | 12/1993 | Galardy | 514/419 |
|---|---|---|---|
| 5,284,827 | 2/1994 | Maione et al. | 514/12 |
| 5,520,914 | 5/1996 | Fett et al. | 424/158.1 |

FOREIGN PATENT DOCUMENTS

| 0462277 | 12/1991 | European Pat. Off. . |
|---|---|---|
| 478101 | 4/1992 | European Pat. Off. . |
| 9112272 | 8/1991 | WIPO . |
| 9210210 | 6/1992 | WIPO . |

OTHER PUBLICATIONS

Bussolino et al., J Cell Biol., vol 119(3), pp. 629–641, 1992.
Behrens et al., EXS, vol. 59, pp. 109–126, 1991.
Weidner, J. Cell. Biol., vol. 111, pp. 2097–2108, 1990.
Tamura et al., *J. Biol. Chem.,* vol. 268(11), pp. 8140–8145, 1993.
Yoshinaga, et al., *Japanese Journal of Cancer Research,* 84(11), 1993, 1150–1158.
Grant et al., *PNAS (USA),* vol. 90, pp. 1937–1941, Mar. 1993.
Bussolino et al., *J. Cell. Biol.,* vol. 119(3), pp. 629–641, Nov. 1992.
Furcht et al., *Lab. Invest.,* vol. 55(5), pp. 505–509, 1986.
Igawa et al., *Biochem. Biophy. Res. Commun.,* vol. 174(2), pp. 831–838, 1991.
Shima et al., *Cell Biol. Int. Rep.,* vol. 15(5), pp. 397–408, 1991.
Gherard et al., *PNAS,* vol. 86, pp. 5844–5848, 1989.
Folkmen et al., *Science,* vol. 235, pp. 442–447, 1989.
Arakaki et al., *Biochem. Biophy. Res. Commun.,* vol. 185(1), pp. 22–28, 1992.
Miyazawa et al., in *Biochem. Biophys. Res. Commun.,* vol. 169, pp. 967–973 (1989).
Nakamura et al., in *Nature (London),* vol. 342, pp. 440–443 (1989).
Grant et al., in *Cell,* vol. 58, pp. 933–943 (1989).
Griffiths et al., in *Am. Acad. Dermatol.,* vol. 20, pp. 617–629 (1989).
Saksela et al., in *Anu. Rev. Cell Biol.,* vol. 4, pp. 93–126 (1988).
Stoker et al., in *J. Cell Sci.,* vol. 77, pp. 209–223 (1985).
Stoker et al., in *Nature (London),* vol. 327, pp. 238–242 (1987).
Folkman et al., in *Adv. Cancer Res.,* vol. 43, pp. 175–203 (1985).
Ingber et al., in *Cell,* vol. 58, pp. 803–805 (1985).
Polson et al., in *Immunol. Commun.,* vol. 9, 495–514 (1980).
Polyverini et al., in *Lab. Invest.,* vol. 51, pp. 635–642 (1984).
Bhargava et al., in *Cell Growth Differ.,* vol. 3, pp. 11–20 (1992).
Weidner et al., in *Proc. Nat'l. Acad. Sci. USA,* vol. 88, pp. 7001–7005 (1991).
Montesano et al., in *Cell,* vol. 67, pp. 901–908 (1991).
Bottaro et al., in *Science,* vol. 251, pp. 802–804 (1991).
Naldini et al., in *Oncogene,* vol. 6, pp. 501–504 (1991).
Rosen et al., in *Cell Motility Factors,* (Birkhauser, Basel) pp. 76–88 (1991).
Rubin et al., in *Proc. Nat'l. Acad. Sci. USA,* vol. 88, pp. 415–419 (1991).
Bhargava et al., in *Cell Motility Factors,* (Birkhauser, Basel) pp. 63–75 (1991).
Rosen et al., in *Proc. Soc. Exp. Biol. Med.,* vol. 195, pp. 34–43 (1990).
Rosen et al., in *In Vitro Cell Dev. Biol.,* vol. 25, pp. 163–173 (1989).

*Primary Examiner*—Chhaya D. Sayala
*Attorney, Agent, or Firm*—Amster, Rothstein & Ebenstein

[57] ABSTRACT

The present invention provides a novel method of inhibiting angiogenesis in a subject by blocking the ability of endogenous scatter factor to promote angiogenesis in the subject. The endogenous scatter factor may be blocked by using an inhibitor to scatter factor, such as an antibody.

3 Claims, 6 Drawing Sheets

Control          SF (20 ng)

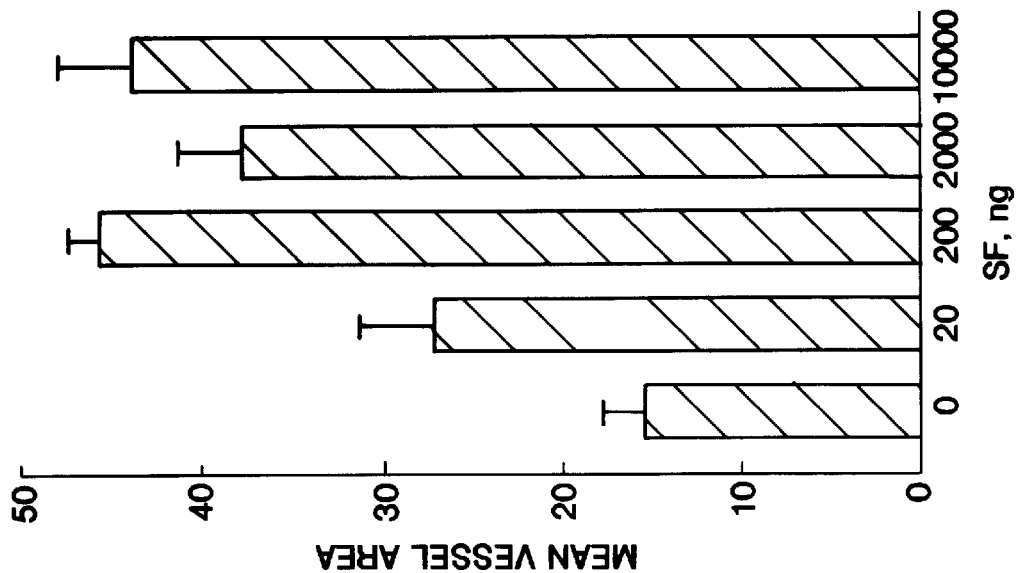
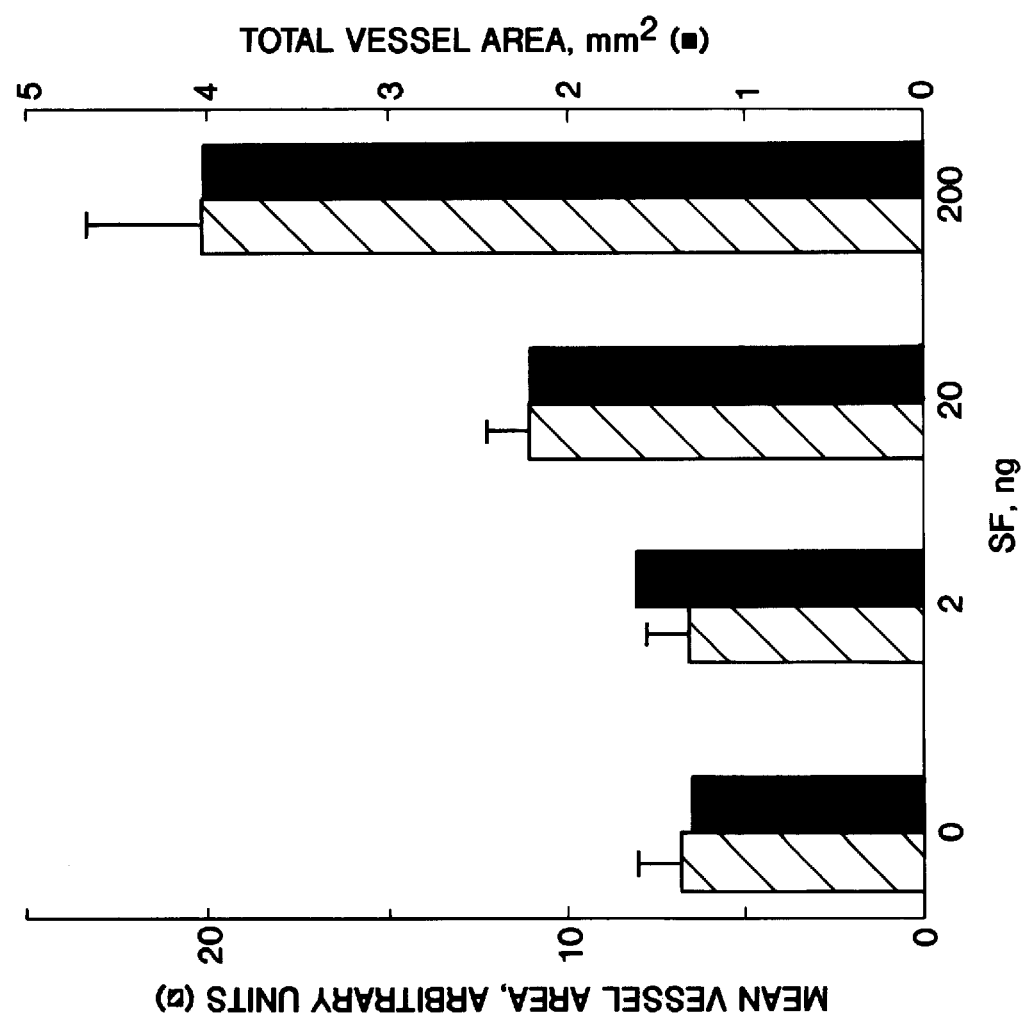

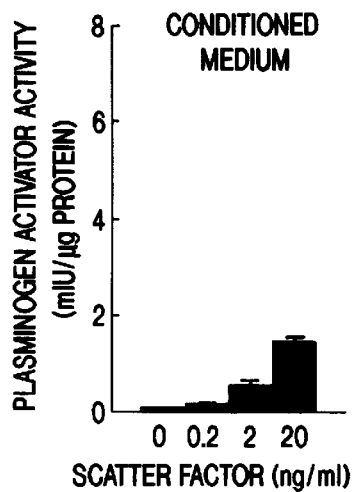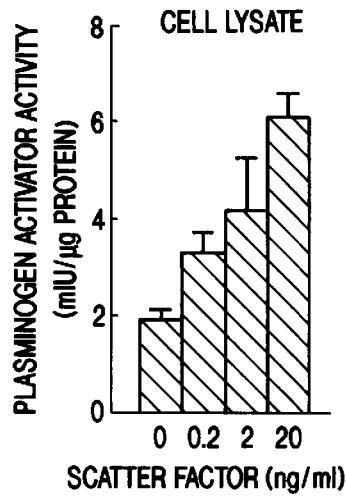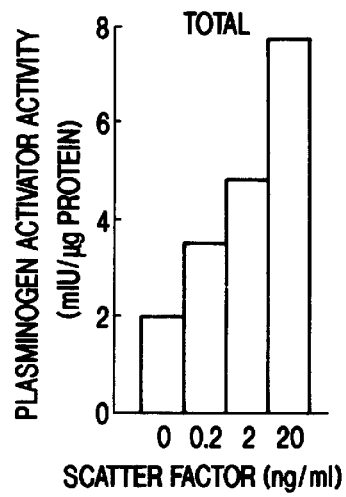
FIG. 4A  FIG. 4B  FIG. 4C
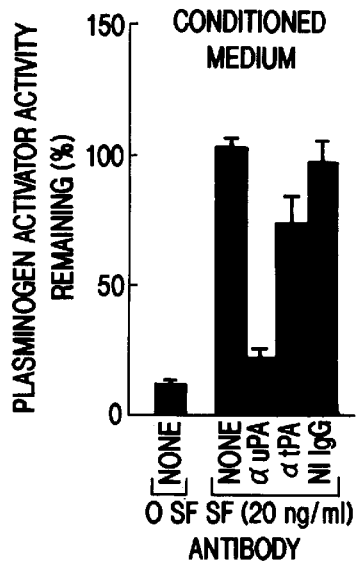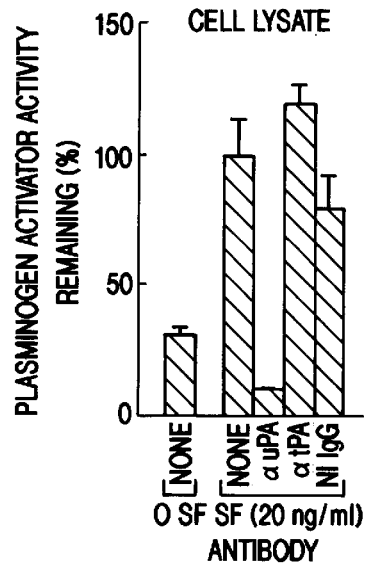
FIG. 4D  FIG. 4E

INHIBITION OF SCATTER FACTOR FOR BLOCKING ANGIOGENESIS

CROSS REFERENCE TO RELATED APPLICATIONS

This application is a continuation of U.S. patent application Ser. No. 08/746,636, filed Nov. 13, 1996, now issued as U.S. Pat. No. 5,837,676, which is a continuation of U.S. patent application Ser. No. 08/138,667, filed Oct. 18, 1993, now abandoned, the contents of each of which are hereby incorporated by reference in their entirety.

STATEMENT OF GOVERNMENT INTEREST

This invention was made with government support under NIH Grant No. CA50516. As such, the government has certain rights in the invention.

FIELD OF THE INVENTION

This invention relates to a method of enhancing wound healing and to a method of enhancing organ transplantation comprising the administration of scatter factor to promote angiogenesis.

BACKGROUND OF THE INVENTION

Scatter factor has previously been described as a cytokine which is secreted by fibroblasts (see Stoker et al., *J. Cell Sci.*, Vol. 77, pp. 209–223 (1985) and Stoker et al., *Nature (London)*, Vol. 327, pp. 238–242 (1987)) and by vascular smooth muscle cells (see Rosen et al., *In Vitro Cell Dev. Biol.*, Vol. 25, pp. 163–173 (1989)). Scatter factor has been shown to disperse cohesive epithelial colonies and stimulate cell motility. In addition, scatter factor has been shown to be identical to hepatocyte growth factor (HGF) (see Weidner et al., *Proc. Nat'l. Acad. Sci. USA*, Vol. 88, pp. 7001–7005 (1991) and Bhargava et al., *Cell Growth Differ.*, Vol. 3, pp. 11–20 (1992)), which is an independently characterized serum mitogen (see Miyazawa et al., *Biochem. Biophys. Res. Commun.*, Vol. 169, pp. 967–973 (1989) and Nakamura et al., *Nature (London)*, Vol. 342, pp. 440–443 (1989)). Scatter factor induces kidney epithelial cells in a collagen matrix to form branching networks of tubules, suggesting that it can also act as a morphogen (see Montesano et al., *Cell*, Vol. 67, pp. 901–908 (1991)).

Scatter factor (HGF) is a basic heparin-binding glycoprotein consisting of a heavy (58 kDa) and a light (31 kDa) subunit. It has 38% amino acid sequence identity with the proenzyme plasminogen (see Nakamura et al., *Nature (London)*, Vol. 342, pp. 440–443 (1989)) and is thus related to the blood coagulation family of proteases. Its receptor in epithelium has been identified as the c-met protooncogene product, a transmembrane tyrosine kinase (see Bottaro et al., *Science*, Vol. 251, pp. 802–804 (1991) and Naldini et al., *Oncogene*, Vol. 6, pp. 501–504 (1991)).

Scatter factor has been found to stimulate endothelial chemotactic and random migration in Boyden chambers (see Rosen et al., *Proc. Soc. Exp. Biol. Med.*, Vol. 195, pp. 34–43 (1990)); migration from carrier beads to flat surfaces (see Rosen et al., *Proc. Soc. ExP. Biol. Med.*, Vol. 195, pp. 34–43 (1990)); formation of capillary-like tubes (see Rosen et al., *Cell Motility Factors*, (Birkhauser, Basel) pp. 76–88 (1991)) and DNA synthesis (see Rubin et al., *Proc. Nat'l. Acad. Sci. USA*, Vol. 88, pp. 415–419 (1991)). In addition, preliminary studies have suggested that scatter factor induces endothelial secretion of plasminogen activators (see Rosen et al., *Cell Motility Factors*, (Birkhauser, Basel) pp. 76–88 (1991)).

The term "angiogenesis", as used herein, refers to the formation of blood vessels. Specifically, angiogenesis is a multistep process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., *Adv. Cancer Res.*, Vol. 43, pp. 175–203 (1985)). These processes are controlled by soluble factors and by the extracellular matrix (see Ingber et al., *Cell*, Vol. 58, pp. 803–805 (1985)).

Because proteases, such as plasminogen activators (the endothelial secretion of which is induced by scatter factor) are required during the early stages of angiogenesis, and since endothelial cell migration, proliferation and capillary tube formation occur during angiogenesis, the inventors hypothesized that scatter factor might enhance angiogenic activity in vivo. In addition, it is desirable to enhance angiogenic activity so that wound healing and organ transplantation can be enhanced.

It is therefore an object of this invention to provide a method of enhancing angiogenic activity.

It is a further object of this invention to provide a method of enhancing wound healing.

It is a still further object of this invention to provide a method of enhancing organ transplantation.

SUMMARY OF THE INVENTION

This invention is directed to a method of promoting angiogenesis comprising the administration of scatter factor. Scatter factor is administered topically, intravenously, intramuscularly, intradermally, subcutaneously or intraperitoneally, and is administered either alone or in combination with a growth factor. Scatter factor can be administered to promote angiogenesis so as to enhance wound healing and organ transplantation.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawing wherein:

FIG. 1 is comprised of FIG. 1A, FIG. 1B, FIG. 1C and FIG. 1D. FIG. 1 represents the result of a murine angiogenesis assay. FIG. 1C shows the quantification by digital image analysis for athymic mice. FIG. 1D shows the quantitation by digital image analysis for C57BL mice;

FIG. 2 is comprised of FIG. 2A, FIG. 2B, FIG. 2C and FIG. 2D. FIG. 2 represents the microscopic appearance of Matrigel plugs.

FIG. 3 is comprised of FIG. 3A, FIG. 3B, FIG. 3C, FIG. 3D and FIG. 3E. FIG. 3 represents scatter factor-induced angiogenesis in rat corneas.

FIG. 4 is comprised of FIG. 4A, FIG. 4B, FIG. 4C, FIG. 4D and FIG. 4E. FIG. 4 represents stimulation of plasminogen activator expression by scatter factor. FIG. 4A shows secreted activity during a 6 hour collection interval. FIG. 4B shows secreted activity intracellularly. FIG. 4C shows total (secreted plus intracellular) activity. FIG. 4D and FIG. 4E show plasminogen activator activity in medium and in lysates from cells treated with scatter factor at 20 ng/ml assayed in the presence of goat anti-human urokinase IgG ($\alpha$uPA), goat anti-human tissue type PA IgG ($\alpha$tPA) or goat nonimmune IgG (NI IgG) (200 $\mu$g/ml), respectively; and FIG. 5 is comprised of FIG. 5A, FIG. 5B, FIG. 5C and FIG. 5D. FIG. 5 represents the results of immunohistochemical staining of skin biopsy samples for scatter factor.

DETAILED DESCRIPTION OF THE INVENTION

Figure 1A:
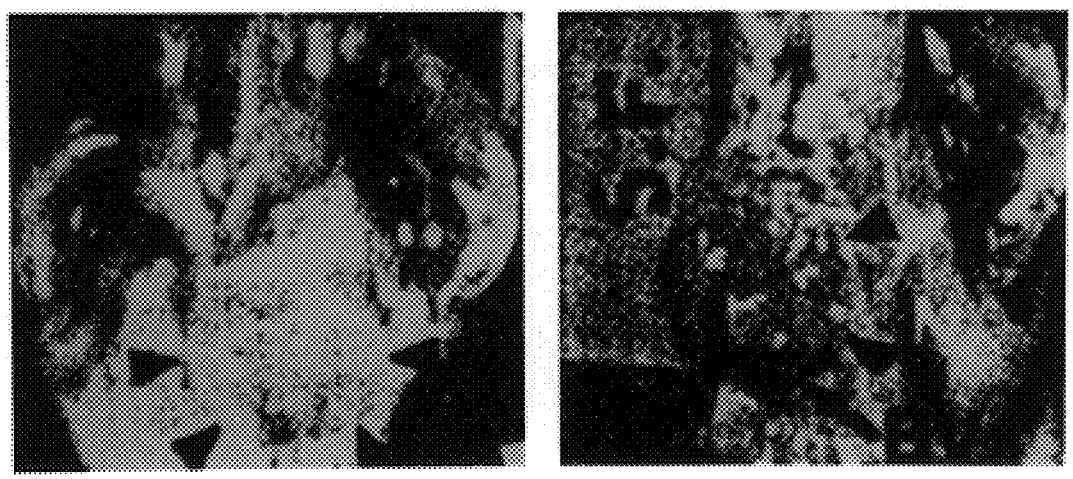
FIG. 1A shows Matrigel plugs (arrowheads) before excision of the plugs.

This invention is directed to a method of promoting angiogenesis by administering scatter factor. Scatter factor can be administered topically, intravenously, intramuscularly, intradermally, subcutaneously or intraperitoneally. The amount of scatter factor to be administered is about 0.1–1000 ng/kg body weight.

Angiogenesis can also be enhanced by administering scatter factor in combination with a growth factor. The growth factor can be selected from the group consisting of TGF-$\alpha$, FGF and PDGF.

The inventors have discovered that angiogenesis is promoted by the administration of scatter factor. Hence, scatter factor can be used to enhance wound healing and organ transplantation, including the transplantation of artificial organs. This invention is therefore directed to a method of enhancing wound healing and to a method of enhancing organ transplantation. In addition, scatter factor can be used to accelerate endothelial cell coverage of vascular grafts in order to prevent graft failure due to reocclusion, and to enhance skin grafting. Further, antibodies to scatter factor can be used to treat tumors and to prevent tumor growth.

In order to prepare scatter factor preparations, mouse scatter factor was purified from serum-free culture medium from ras-transformed NIH/23T3 cells (clone D4) by cation-exchange chromatography as described by Rosen et al., *Proc. Soc. Exp. Biol. Med.*, Vol. 195, pp. 34–43 (1990), followed by immunoaffinity chromatography and ultrafiltration. Recombinant human HGF (rhHGF) was provided by Toshikazu Nakamura (Kyushu University, Fukuoka, Japan). Scatter factor (HGF) is commercially available from Collaborative Research, Bedford, Mass.

In order to make the antibody preparations, antisera to native human placental scatter factor and rhHGF were prepared by immunizing rabbits with purified factors (see Bhargava et al., *Cell Growth Differ.*, Vol. 3, pp. 11–20 (1992) and Bhargava et al., *Cell Motility Factors*, (Birkhauser, Basel) pp. 63–75 (1991)). A chicken egg yolk antibody to human placental scatter factor was prepared by immunizing two White Leghorn hens, 22–24 weeks old, with 500 $\mu$g of human placental scatter factor emulsified in complete Freund's adjuvant. Booster injections were given 14 to 28 days later, and the eggs were collected daily. The IgG fraction from seven eggs was extracted and partially purified by the methods described by Polson et al., *Immunol. Commun.*, Vol. 9, pp. 495–514 (1980). The final preparation contained 80 $\mu$g of protein per ml in phosphate-buffered saline (PBS). Antibody specificity was established by recognition of mouse and human scatter factors on immunoblots, specific binding of scatter factor to antibody-Sepharose columns, and inhibition of the in vitro biologic activities of mouse and human scatter factor.

In order to perform plasminogen activator assays, bovine brain microvessel endothelial cells (BBEC) were isolated from brain cortex after removal of the pia mater, identified as endothelial, and cultured by standard techniques. BBEC (passage 10–12) at about 80% confluency in 60 mm Petri dishes were treated with mouse scatter factor for 24 hours, washed, and incubated for 6 hours in 2.5 ml of serum-free Dulbecco's modified Eagle's medium (DMEM) to collect secreted proteins. The cells were washed, scraped into PBS, collected in 0.5 ml of PBS by centrifugation, and lysed by sonication. Aliquots of medium and cell lysates were assayed for PA activity by a two-step chromogenic reaction as described by Coleman et al., *Ann. N.Y. Acad. Sci.*, Vol. 370, pp. 617–626 (1991). Human high molecular weight urokinase (American Diagnostica, Greenwich, Conn.) was used as the standard. The protein content of the lysate was determined by using the Bradford dye-binding assay (Bio-Rad).

In order to perform the murine angiogenesis assay, angiogenesis was assayed as growth of blood vessels from subcutaneous tissue into a solid gel of basement membrane containing the test sample. Matrigel (7 mg in 0.5 ml; Collaborative Research) in liquid form at 4° C. was mixed with scatter factor and injected into the abdominal subcutaneous tissues of athymic XID nude beige mice or C57BL/6 mice. Matrigel rapidly forms a solid gel at body temperature, trapping the factor to allow slow release and prolonged exposure to surrounding tissues. After 10 days, the mice were sacrificed and the Matrigel plugs were excised and fixed in 4% formaldehyde in phosphate buffer. Plugs were embedded in paraffin, sectioned, stained with Masson's trichrome (which stains endothelial cells reddish-purple and stains the Matrigel violet or pale green), and examined for ingrowth of blood vessels. Vessel formation was quantitated from stained sections using the Optimax digital image analyzer connected to an Olympus microscope (see Grant et al., *Cell*, Vol. 58, pp. 933–943 (1989)). Results were expressed as mean vessel area per field ±SEM (arbitrary units) or as total vessel area (mm$^2$) in 20 random fields.

In order to perform the rat cornea angiogenesis assay, angiogenesis was assayed in the avascular rate cornea, as described by Polverini et al., *Lab. Invest.*, vol. 51, pp. 635–642 (1984). Test samples were combined 1:1 with a sterile solution of Hydron (Interferon Laboratories, New Brunswick, N.J.) and air-dried overnight. A 5 $\mu$l pellet was inserted into a surgically created pocket in the corneal stroma and positioned 1–1.5 mm from the limbus. Corneas were examined daily with a dissecting microscope for up to 7 days for capillary growth. Assay responses were scored as positive if sustained directional ingrowth of capillary sprouts and hairpin loops occurred during the observation period. Responses were scored as negative either when no neovascularization was detected or when only an occasional sprout or hairpin loop was observed that showed no evidence of sustained directional ingrowth. After 7 days, corneas were perfused with colloidal carbon, and whole-mount preparations were examined and photographed.

To study immunohistochemistry, five-micrometer-thick cryostat sections were prepared from biopsy samples of plaques or of areas of normal skin in patients with active psoriasis. The sections were stained by using an avidin-biotin immunoperoxidase technique (see Griffiths et al., *Am. Acad. Dermatol.*, Vol. 20, pp. 617–629 (1989)). The chromogen was Texas red conjugated to avidin. The primary antibody was rabbit polyclonal antiserum to purified native human placental scatter factor or to rhHGF (1:1000 dilution). Nonimmune rabbit serum (1:1000) was used as a negative control.

Figure 1B:
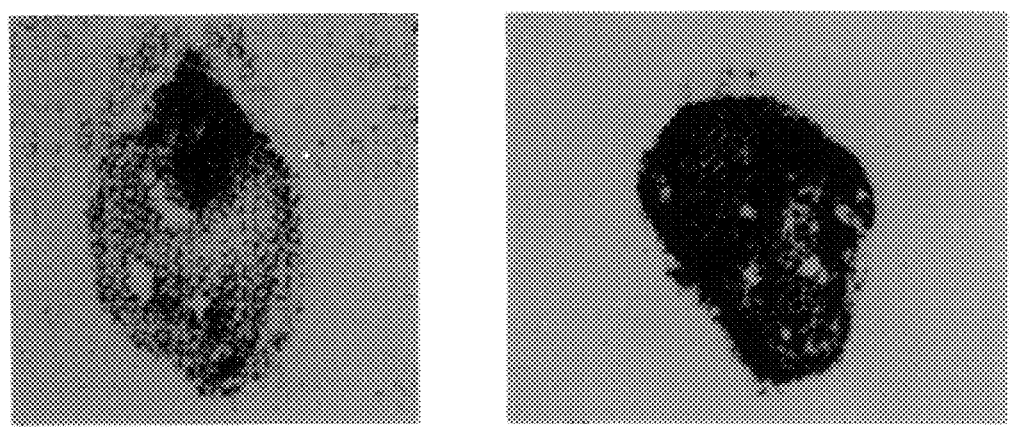
FIG. 1B shows plugs (arrowheads) after excision of the plugs.

Two different in vivo assays were used to evaluate the angiogenic activity of mouse scatter factor. In the first assay, the murine angiogenesis assay, samples mixed with Matrigel, a matrix of reconstituted basement membrane, were injected subcutaneously into mice. After 10 days, the mice were sacrificed for histologic and morphometric analysis of Matrigel plugs. Control plugs were found to be pale pink, while plugs containing scatter factor were found to be bright red and often contained superficial blood vessels (see FIG. 1A and FIG. 1B).

Figure 2A:
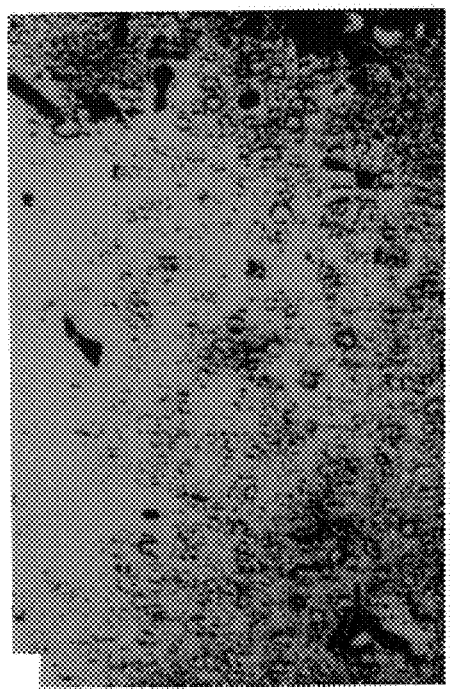
FIG. 2A represents sections of plugs from athymic control (0 ng scatter factor) mice.
Figure 2B:
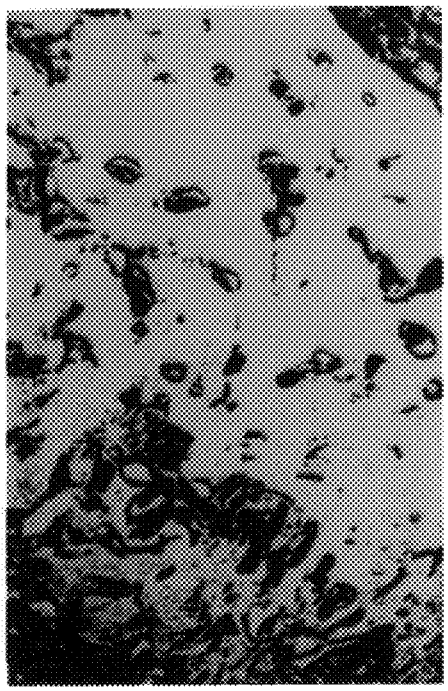
FIG. 2B represents sections of plugs from athymic mice which contain 2 ng scatter factor.
Figure 2C:
FIG. 2C represents sections of plugs from athymic mice which contain 20 ng scatter factor.
Figure 2D:
FIG. 2D represents sections of plugs from athymic mice which contain 200 ng of scatter factor.

Histologic analysis showed little cellularity in control plugs (see FIG. 2A). Plugs containing 2 ng of scatter factor often had increased numbers of cells (see FIG. 2B), 90% of which stained for factor VIII antigen, an endothelial cell marker (not shown). At 20 ng of scatter factor, cell number was increased, and vessels were present (FIG. 2C). At 200 ng of scatter factor, plugs were even more cellular, with endothelial cells making up 50–60% of the cell population. Many large vessels containing smooth muscle cells were seen (see FIG. 2D).

Morphometric analysis of vessel area (see Grant et al., *Cell*, Vol. 58, pp. 933–943 (1989)) revealed a dose-dependent angiogenic response in athymic (FIG. 1C) and C57BL (FIG. 1D) mice, with half-maximal and maximal responses at about 20 and 200 ng, respectively. Histologic examination at day 10 showed no evidence of inflammation in scatter factor-containing plugs in athymic mice. In C57BL, no inflammation was observed at ≦200 ng of scatter factor, but leukocytic infiltration was present in tissue surrounding the plugs at ≦2000 ng of scatter factor.

Figure 3A:
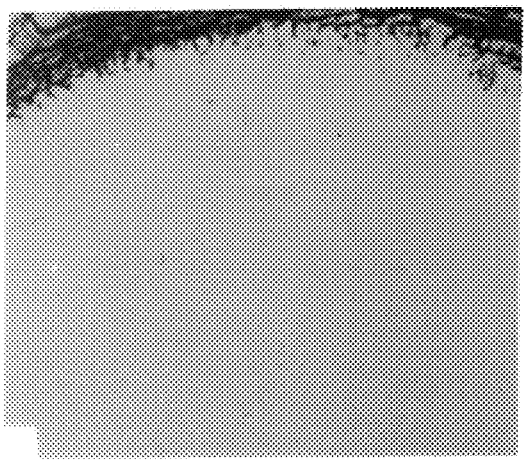
As shown in FIG. 3A, no angiogenic response was observed in control pellets containing PBS.
Figure 3B:
As shown in FIG. 3B, the response for 50 ng scatter factor was positive but weak in comparison with high concentrations of scatter factor.
Figure 3C:
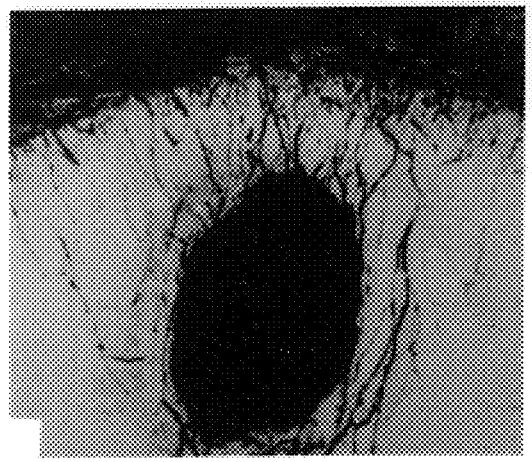
As shown in FIG. 3C, and FIG. 3D, scatter factor concentrations of 100 ng and 500 ng, respectively, gave strong positive responses.
Figure 3D:
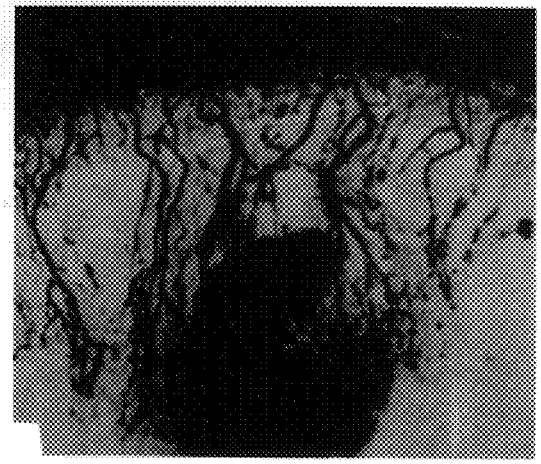
Figure 3E:
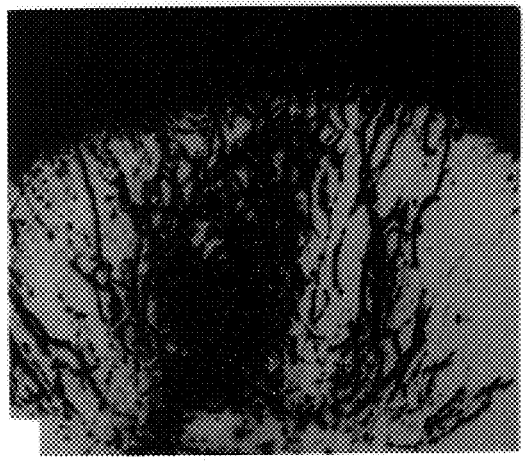
FIG. 3E shows a strong angiogenic response which was induced by 150 ng of basic FGF, a positive control.

In the second assay, samples were implanted in the avascular rat cornea to allow ingrowth of blood vessels from the limbus. Control implants gave no positive responses (see Table 1, below, and FIG. 3A), while implants containing mouse scatter factor induced a dose-dependent corneal neovascularization. Responses at 50 ng (FIG. 3B) were reduced in intensity compared with those at 100 and 500 ng (FIG. 3C and FIG. 3D, respectively). The maximal response to scatter factor was observed at doses of ≦100 ng and was similar to the response to 150 ng of human basic FGF, a positive control (see FIG. 3E).

TABLE 1

Neovascular responses induced in rat corneas by scatter factor (SF)

| Content of pellet | Corneal neovascularization | |
|---|---|---|
| | Positive responses | % |
| Negative controls | | |
| Sham implant | 0/3 | 0 |
| Hydron | 0/2 | 0 |
| PBS | 0/2 | 0 |
| Positive control | | |
| Basic FGF (150 ng) | 4/4 | 100 |
| scatter factor (SF) | | |
| 5 ng | 0.4 | 0 |
| 50 ng | 3/5* | 60 |
| 100 ng | 5/5 | 100 |
| 500 ng | 5/5 | 100 |
| 1000 ng | 5/5+ | 100 |

*Responses were much weaker in intensity compared with implants containing 100 or 500 ng of scatter factor.
+Corneas showed significant inflammation.

rhHGF also induced angiogenesis in the rat cornea (see Table 2, below). At 100 ng, positive responses were observed in four of five implants. At 500 ng of rhHGF, all five implants gave positive responses. Chicken and rabbit antibodies to human placental scatter factor strongly inhibited the angiogenic responses to mouse scatter factor and rhHGF, but not to basic FGF (see Table 2).

TABLE 2

Neovascular responses induced in rat corneas by native mouse scatter factor (SF) and rhHGF with or without antibody (Ab)

| Content of pellet | Corneal neovascularization | |
|---|---|---|
| | Positive responses | % |
| Controls | | |
| Hydron + PBS | 0/8 | 0 |
| Chicken Ab | 0/4 | 0 |
| Rabbit Ab (Ab 978) | 0/3 | 0 |
| Basic FGF (150 ng) | 3/3 | 100 |
| Basic FGF (150 ng) + rabbit Ab | 3/3 | 100 |
| Factor ± Ab | | |
| Mouse SF (100 ng) | 3/3 | 100 |
| Mouse SF (100 ng) + chicken Ab | 1/5* | 20 |
| rhHGF (100 ng) | 4/5 | 80 |
| rhHGF (500 ng) | 5/5+ | 100 |
| rhHGF (100 ng) + chicken Ab | 2/5* | 33 |
| rh HGF (100 ng) + rabbit Ab | 0/5 | 0 |

Antibodies were diluted in PBS. Final dilutions after mixing with Hydron were 1:20 for the chicken antibodies and 1:200 for the rabbit antibodies.
*Responses scored as positive were very weak.
+This concentration of rhHGF was inflammatory.

To assess inflammation, corneas were examined by direct stereomicroscopy daily for the duration of the experiments. Corneas chosen at random were examined histologically at 6, 12 and 24 hours and at 3, 5, and 7 days after implantation of scatter factor and control pellets. Inflammation was not detected at lower angiogenic doses of scatter factor (50–500 ng of mouse scatter factor, 100 ng of rhHGF). At higher doses (50–500 ng of mouse scatter factor, 500 ng of rhHGF), a prominent inflammatory infiltrate was observed. The majority of cells were monocytes and macrophages, as judged by morphology and immunostaining for F4/80, a macrophage/monocyte marker.

Plasminogen activators convert plasminogen into plasmin, a potent serine protease that lyses fibrin clots, degrades components of extracellular matrix, and activates enzymes (e.g., procollagenases) that further degrade matrix (see Saksela et al., *Anu. Rev. Cell Biol.*, Vol. 4, pp. 93–126 (1988)). The inventors have discovered that scatter factor induces large dose-dependent increases in secreted (see FIG. 4A) and cell-associated (see FIG. 4B) plasminogen activator activity in microvascular endothelium (BBEC). Total plasminogen activator activity (secreted plus cell-associated) was increased 4-fold relative to control when scatter factor was present at 20 ng/ml ($\cong 0.2$ nM). Similar results were obtained in large vessel endothelium (not shown). Most of the secreted and cell-associated plasminogen activator activity in BBEC was blocked by antibodies to urokinase, but not by antibodies to tissue plasminogen activator (see FIG. 4D and FIG. 4E).

Figure 5A:
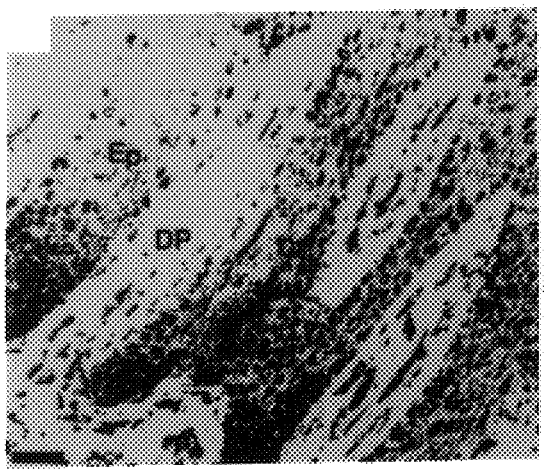
FIG. 5A, FIG. 5B and FIG. 5C show immunohistochemical staining of psoriatic plaques.
Figure 5B:
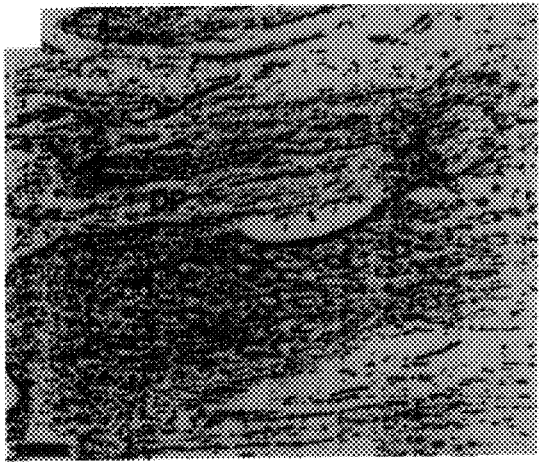
Figure 5C:
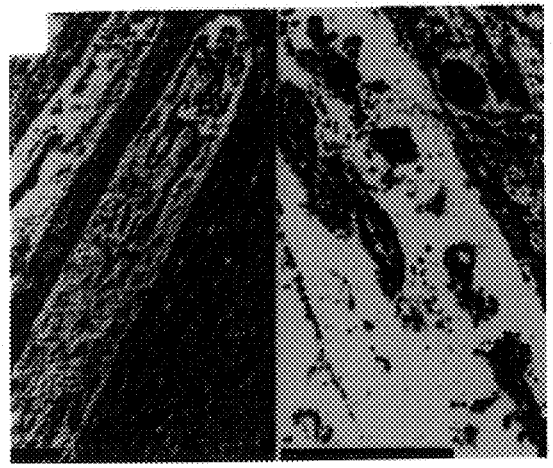
Figure 5D:
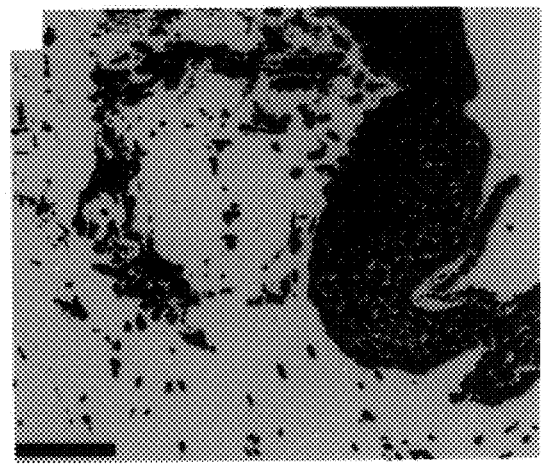
FIG. 5D shows immunohistochemical staining of normal skin from a patient with psoriasis.

Angiogenesis is often associated with chronic inflammation diseases. Psoriasis is a common inflammatory skin disease characterized by prominent epidermal hyperplasia and neovascularization in the dermal papillae. Frozen sections of biopsy samples from psoriatic plaques from 10 patients each showed positive immunohistochemical staining for scatter factor in spindle-shaped and mononuclear cells within the dermal papillae and papillary dermis. Antisera to human placental scatter factor and rhHGF gave an identical staining pattern, as illustrated in FIG. 5A. Scatter factor-positive cells were arranged in a perivascular distribution. Cells of the blood vessel wall did not stain for scatter factor (see FIG. 5C). Normal skin from psoriasis patients or from normal subjects showed little or no staining for scatter factor (FIG. 5D). Sections from psoriatic plaques treated with nonimmune serum as the primary antibody (negative control) showed no staining (FIG. 5B).

Hence, the inventors have determined that physiologic quantities of scatter factor [100–200 ng ($\cong$1–2 pmol)] induced strong angiogenic responses in two in vivo assays. It is likely that this angiogenic activity is due, in part, to direct effects on endothelium since: (i) scatter factor stimulates endothelial migration, proliferation, and tube formation in vitro; (ii) histologic studies showed no evidence of inflammation at scatter factor doses that gave strong angiogenic responses; and (iii) anti-scatter factor antibodies blocked the angiogenic responses. The inventors also found that scatter factor stimulates endothelial cell expression of urokinase. Urokinase, bound to its specific cells surface receptor, is thought to mediate focal, directed, extracellular proteolysis, which is required for endothelial cell invasion and migration during the early stages of angiogenesis.

Growth factors TGFB, FGF, and platelet-derived growth factor (PDGF) are present in Matrigel and in the matrices of several tissues, including the cornea. The inventors have discovered that combinations of scatter factor and either TGFB, FGF, or PDGF provide greater stimulation of endothelial tube formation in vitro than did the same agents used individually. The concentrations studied (1 ng/ml) were about 10 times those found in 250 μg of Matrigel, and scatter factor strongly stimulated tube formation on its own, by up to 8 times the amount stimulated by the control.

The major scatter factor producer cells are fibroblasts, smooth muscle cells, and leukocytes. With rare exceptions, responder cells (epithelium, endothelium, melanocytes) are nonproducers. The immunohistochemical studies of psoriatic plaques suggest that scatter factor is produced by cells located outside of the blood vessel wall. Studies by the inventors have indicated that cultured endothelial cells express c-met mRNA and that immunoreactive c-met protein is present in blood vessel wall cells (endothelium and pericytes) in psoriatic plaques. This suggests that scatter factor may play a role in microvessel formation or elongation in psoriasis and that its likely mode of action is paracrine.

Scatter factor (HGF) stimulates motility, invasiveness, proliferation, and morphogenesis of epithelium, and it may be involved in physiologic and pathologic processes such as embryogenesis, wound healing, organ regeneration, inflammation, and tumor invasion. Angiogenesis is a component of each of these processes. Therefore, the in vivo biologic action of scatter factor may be due, in part, to its effects on both epithelial and vascular endothelial cells.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method of treating a tumor in a subject comprising administering to the subject an agent effective to block the ability of endogenous scatter factor to promote angiogenesis in the tumor in the subject.

2. The method of claim 1, wherein the agent is an inhibitor to scatter factor.

3. A method of treating a tumor in a subject comprising administering to the subject an antibody to scatter factor in an amount effective to block the ability of endogenous scatter factor to promote angiogenesis in the tumor in the subject.

* * * * *